(12) United States Patent
    Burns

(10) Patent No.: US 12,642,481 B2
(45) Date of Patent: Jun. 2, 2026

(54) SEM TREND ANALYSIS

(71) Applicant: Bruin Biometrics, LLC, Los Angeles, CA (US)

(72) Inventor: Martin F. Burns, Los Angeles, CA (US)

(73) Assignee: Bruin Biometrics, LLC, Los Angeles, CA (US)

( * ) Notice: Subject to any disclaimer, the term of this patent is extended or adjusted under 35 U.S.C. 154(b) by 0 days.

(21) Appl. No.: 18/612,918

(22) Filed: Mar. 21, 2024

(65) Prior Publication Data

US 2024/0225529 A1 Jul. 11, 2024

Related U.S. Application Data

(63) Continuation of application No. 16/213,664, filed on Dec. 7, 2018, now abandoned.

(60) Provisional application No. 62/623,857, filed on Jan. 30, 2018, provisional application No. 62/596,089, filed on Dec. 7, 2017.

(51) Int. Cl.
    *A61B 5/00* (2006.01)
(52) U.S. Cl.
    CPC .............. *A61B 5/443* (2013.01); *A61B 5/445* (2013.01); *A61B 5/447* (2013.01); *A61B 5/7275* (2013.01); *A61B 5/7282* (2013.01)
(58) Field of Classification Search
    CPC ......... A61B 5/443; A61B 5/445; A61B 5/447; A61B 5/7275; A61B 5/7282; A61B 5/0537; G16H 50/30
    See application file for complete search history.

(56) References Cited

U.S. PATENT DOCUMENTS

| | | | |
|---|---|---|---|
| 3,851,641 A | 12/1974 | Toole et al. |
| 4,295,009 A | 10/1981 | Weidler |
| 4,557,271 A | 12/1985 | Stoller et al. |
| 4,857,716 A | 8/1989 | Gombrich et al. |
| 4,860,753 A | 8/1989 | Amerena |
| 5,001,436 A | 3/1991 | Scot |
| 5,073,126 A | 12/1991 | Kikuchi et al. |

(Continued)

FOREIGN PATENT DOCUMENTS

| | | |
|---|---|---|
| AU | 2020103438 A4 | 1/2021 |
| CA | 2811609 | 11/2011 |

(Continued)

OTHER PUBLICATIONS

Moore Z, Patton D, Rhodes SL, O'Connor T. Subepidermal moisture (SEM) and bioimpedance: a literature review of a novel method for early detection of pressure-induced tissue damage (pressure ulcers). Int Wound J. Apr. 2017;14(2):331-337. (Year: 2016).*

(Continued)

*Primary Examiner* — Michael R Bloch
(74) *Attorney, Agent, or Firm* — Arnold & Porter Kaye Scholer LLP

(57) ABSTRACT

The present disclosure provides for, and includes, a method of detecting tissue damage before it is visible on a patient's skin, comprising: measuring a plurality of sub-epidermal moisture (SEM) values at a single location at incremental times, calculating a slope between the latest SEM value and the immediately prior SEM value, comparing this slope to a threshold value, and determining that there is tissue damage if the slope exceeds the threshold value.

6 Claims, 6 Drawing Sheets

(56)  References Cited

U.S. PATENT DOCUMENTS

| | | |
|---|---|---|
| 5,152,296 A | 10/1992 | Simons |
| 5,284,150 A | 2/1994 | Butterfield et al. |
| 5,292,341 A | 3/1994 | Snell |
| 5,367,789 A | 11/1994 | Lamont |
| 5,815,416 A | 9/1998 | Liebmann et al. |
| 5,904,581 A | 5/1999 | Pope et al. |
| 6,148,098 A | 11/2000 | Rutschke et al. |
| 6,185,452 B1 | 2/2001 | Schulman |
| 6,204,749 B1 | 3/2001 | Ishihara |
| 6,223,088 B1 | 4/2001 | Scharnberg et al. |
| 6,254,435 B1 | 7/2001 | Cheong et al. |
| 6,312,263 B1 | 11/2001 | Higuchi et al. |
| 6,330,479 B1 | 12/2001 | Stauffer |
| 6,368,284 B1 | 4/2002 | Bardy |
| 6,370,426 B1 | 4/2002 | Campbell et al. |
| 6,434,422 B1 | 8/2002 | Tomoda et al. |
| 6,577,700 B1 | 6/2003 | Fan et al. |
| 6,634,045 B1 | 10/2003 | DuDonis et al. |
| 6,646,556 B1 | 11/2003 | Smith et al. |
| 6,738,798 B1 | 5/2004 | Ploetz et al. |
| 6,756,793 B2 | 6/2004 | Hirono et al. |
| 6,963,772 B2 | 11/2005 | Bloom et al. |
| 7,079,899 B2 | 7/2006 | Petrofsky |
| 7,291,023 B1 | 11/2007 | Still et al. |
| 7,315,767 B2 | 1/2008 | Caduff et al. |
| 7,402,135 B2 | 7/2008 | Leveque et al. |
| 7,783,344 B2 | 8/2010 | Lackey et al. |
| 8,011,041 B2 | 9/2011 | Hann |
| 8,060,315 B2 | 11/2011 | Brosette et al. |
| 8,355,925 B2 | 1/2013 | Rothman et al. |
| 8,390,583 B2 | 3/2013 | Forutanpour et al. |
| 8,494,617 B2 | 7/2013 | Baker, Jr. et al. |
| 8,648,707 B2 | 2/2014 | Franz et al. |
| 8,690,785 B2 | 4/2014 | Lading |
| 8,724,833 B1 | 5/2014 | Shain et al. |
| 8,925,392 B2 | 1/2015 | Esposito et al. |
| 9,028,407 B1 | 5/2015 | Bennett-Guerrero |
| 9,095,305 B2 | 8/2015 | Engler et al. |
| 9,220,455 B2 | 12/2015 | Sarrafzadeh et al. |
| 9,271,676 B2 | 3/2016 | Alanen et al. |
| 9,398,879 B2 | 7/2016 | Sarrafzadeh et al. |
| 9,675,289 B2 | 6/2017 | Heaton |
| 9,763,596 B2 | 9/2017 | Tonar et al. |
| 9,949,683 B2 | 4/2018 | Afentakis |
| 9,980,673 B2 | 5/2018 | Sarrafzadeh et al. |
| 10,085,643 B2 | 10/2018 | Bandic et al. |
| 10,126,340 B2 | 11/2018 | Simmons |
| 10,166,387 B2 | 1/2019 | Bergelin et al. |
| 10,178,961 B2 | 1/2019 | Tonar et al. |
| 10,182,740 B2 | 1/2019 | Tonar et al. |
| 10,188,340 B2 | 1/2019 | Sarrafzadeh et al. |
| 10,194,856 B2 | 2/2019 | Afentakis et al. |
| 10,206,604 B2 | 2/2019 | Bergelin et al. |
| 10,226,187 B2 | 3/2019 | Al-Ali et al. |
| 10,278,636 B2 | 5/2019 | Wu et al. |
| 10,285,898 B2 | 5/2019 | Douglas et al. |
| 10,307,060 B2 | 6/2019 | Tran |
| 10,342,482 B1 | 7/2019 | Lisy et al. |
| 10,383,527 B2 | 8/2019 | Al-Ali |
| 10,420,602 B2 | 9/2019 | Horton et al. |
| 10,441,185 B2 | 10/2019 | Rogers et al. |
| 10,448,844 B2 | 10/2019 | Al-Ali et al. |
| 10,463,293 B2 | 11/2019 | Maharbiz et al. |
| 10,485,447 B2 | 11/2019 | Tonar et al. |
| 10,881,157 B1 | 1/2021 | Anderson et al. |
| 10,898,129 B2 | 1/2021 | Burns et al. |
| 10,950,960 B2 | 3/2021 | Burns et al. |
| 10,959,664 B2 | 3/2021 | Burns et al. |
| 11,172,871 B2 | 11/2021 | Bly et al. |
| 11,191,477 B2 | 12/2021 | Burns |
| 11,253,192 B2 | 2/2022 | Sarrafzadeh et al. |
| 11,284,810 B2 | 3/2022 | Tonar et al. |
| 11,304,652 B2 | 4/2022 | Burns et al. |
| 11,337,651 B2 | 5/2022 | Burns et al. |
| 11,342,696 B2 | 5/2022 | Burns et al. |
| 11,426,118 B2 | 8/2022 | Burns |
| 11,471,094 B2 | 10/2022 | Burns et al. |
| 11,534,077 B2 | 12/2022 | Tonar et al. |
| 11,600,939 B2 | 3/2023 | Burns et al. |
| 11,627,910 B2 | 4/2023 | Burns et al. |
| 11,642,075 B2 | 5/2023 | Burns et al. |
| 11,779,265 B2 | 10/2023 | Sarrafzadeh et al. |
| 11,824,291 B2 | 11/2023 | Burns et al. |
| 11,832,929 B2 | 12/2023 | Tonar et al. |
| 11,901,080 B1 | 2/2024 | Matt et al. |
| 11,980,475 B2 | 5/2024 | Burns et al. |
| 12,097,041 B2 | 9/2024 | Burns et al. |
| 12,132,271 B2 | 10/2024 | Burns et al. |
| 2001/0049609 A1 | 12/2001 | Girouard et al. |
| 2001/0051783 A1 | 12/2001 | Edwards et al. |
| 2002/0016535 A1 | 2/2002 | Martin et al. |
| 2002/0032485 A1 | 3/2002 | Flam et al. |
| 2002/0070866 A1 | 6/2002 | Newham |
| 2002/0112898 A1 | 8/2002 | Honda et al. |
| 2002/0143262 A1 | 10/2002 | Bardy |
| 2003/0009244 A1 | 1/2003 | Engleson et al. |
| 2003/0036674 A1 | 2/2003 | Bouton |
| 2003/0036713 A1 | 2/2003 | Bouton et al. |
| 2003/0110662 A1 | 6/2003 | Gilman et al. |
| 2003/0116447 A1 | 6/2003 | Surridge et al. |
| 2003/0130427 A1 | 7/2003 | Cleary et al. |
| 2003/0139255 A1 | 7/2003 | Lina |
| 2003/0199783 A1 | 10/2003 | Bloom et al. |
| 2004/0041029 A1 | 3/2004 | Postman et al. |
| 2004/0046668 A1 | 3/2004 | Smith et al. |
| 2004/0054298 A1 | 3/2004 | Masuo et al. |
| 2004/0080325 A1 | 4/2004 | Ogura |
| 2004/0133092 A1 | 7/2004 | Kain |
| 2004/0147977 A1 | 7/2004 | Petrofsky |
| 2004/0171962 A1 | 9/2004 | Leveque et al. |
| 2004/0176754 A1 | 9/2004 | Island et al. |
| 2004/0236200 A1 | 11/2004 | Say et al. |
| 2004/0254457 A1 | 12/2004 | Van Der Weide |
| 2005/0027175 A1 | 2/2005 | Yang |
| 2005/0049658 A1 | 3/2005 | Connors et al. |
| 2005/0070778 A1 | 3/2005 | Lackey et al. |
| 2005/0086072 A1 | 4/2005 | Fox et al. |
| 2005/0096513 A1 | 5/2005 | Ozguz et al. |
| 2005/0177061 A1 | 8/2005 | Alanen et al. |
| 2005/0203435 A1 | 9/2005 | Nakada |
| 2005/0215918 A1 | 9/2005 | Frantz et al. |
| 2005/0245795 A1 | 11/2005 | Goode et al. |
| 2005/0251418 A1 | 11/2005 | Fox et al. |
| 2006/0052678 A1 | 3/2006 | Drinan et al. |
| 2006/0058593 A1 | 3/2006 | Drinan et al. |
| 2006/0097949 A1 | 5/2006 | Luebke et al. |
| 2006/0184034 A1 | 8/2006 | Haim et al. |
| 2006/0206013 A1 | 9/2006 | Rothman et al. |
| 2006/0239547 A1 | 10/2006 | Robinson et al. |
| 2006/0247514 A1 | 11/2006 | Panasyuk et al. |
| 2007/0043282 A1 | 2/2007 | Mannheimer et al. |
| 2007/0051362 A1 | 3/2007 | Sullivan et al. |
| 2007/0106172 A1 | 5/2007 | Abreu |
| 2007/0179585 A1 | 8/2007 | Chandler et al. |
| 2007/0185392 A1 | 8/2007 | Sherman et al. |
| 2007/0191273 A1 | 8/2007 | Ambati et al. |
| 2007/0213700 A1 | 9/2007 | Davison et al. |
| 2007/0248542 A1 | 10/2007 | Kane et al. |
| 2007/0276359 A1 | 11/2007 | Segal et al. |
| 2008/0009764 A1 | 1/2008 | Davies |
| 2008/0015894 A1 | 1/2008 | Miller et al. |
| 2008/0027509 A1 | 1/2008 | Andino et al. |
| 2008/0039700 A1 | 2/2008 | Drinan et al. |
| 2008/0048680 A1 | 2/2008 | Hargreaves et al. |
| 2008/0054276 A1 | 3/2008 | Vogel et al. |
| 2008/0063363 A1 | 3/2008 | Kientz et al. |
| 2008/0166268 A1 | 7/2008 | Yamaguchi et al. |
| 2008/0259577 A1 | 10/2008 | Hu et al. |
| 2008/0278336 A1 | 11/2008 | Ortega et al. |
| 2009/0047694 A1 | 2/2009 | Shuber |
| 2009/0054752 A1 | 2/2009 | Jonnalagadda et al. |
| 2009/0076410 A1 | 3/2009 | Libbus et al. |
| 2009/0104797 A1 | 4/2009 | Tseng et al. |
| 2009/0124924 A1 | 5/2009 | Eror et al. |

(56) References Cited

U.S. PATENT DOCUMENTS

| | | |
|---|---|---|
| 2009/0189092 A1 | 7/2009 | Aoi et al. |
| 2009/0209830 A1 | 8/2009 | Nagle et al. |
| 2009/0285785 A1 | 11/2009 | Jimi et al. |
| 2009/0301200 A1 | 12/2009 | Tanaka et al. |
| 2009/0306487 A1 | 12/2009 | Crowe et al. |
| 2009/0326346 A1 | 12/2009 | Kracker et al. |
| 2010/0017182 A1 | 1/2010 | Voros et al. |
| 2010/0030167 A1 | 2/2010 | Thirstrup et al. |
| 2010/0042389 A1 | 2/2010 | Farruggia et al. |
| 2010/0073170 A1 | 3/2010 | Siejko et al. |
| 2010/0090680 A1 | 4/2010 | Banhegyesi |
| 2010/0113979 A1 | 5/2010 | Sarrafzadeh et al. |
| 2010/0152551 A1 | 6/2010 | Hsu et al. |
| 2010/0268111 A1 | 10/2010 | Drinan et al. |
| 2010/0298687 A1 | 11/2010 | Yoo et al. |
| 2010/0312076 A1 | 12/2010 | Bly et al. |
| 2010/0312233 A1 | 12/2010 | Furnish et al. |
| 2010/0324455 A1 | 12/2010 | Rangel et al. |
| 2010/0324611 A1 | 12/2010 | Deming et al. |
| 2011/0015697 A1 | 1/2011 | McAdams |
| 2011/0046505 A1 | 2/2011 | Cornish et al. |
| 2011/0160548 A1 | 6/2011 | Forster |
| 2011/0175844 A1 | 7/2011 | Berggren |
| 2011/0184264 A1 | 7/2011 | Galasso et al. |
| 2011/0191122 A1 | 8/2011 | Kharraz Tavakol et al. |
| 2011/0223078 A1 | 9/2011 | Ohashi |
| 2011/0237926 A1 | 9/2011 | Jensen |
| 2011/0263950 A1 | 10/2011 | Larson et al. |
| 2011/0301441 A1 | 12/2011 | Bandic et al. |
| 2011/0313311 A1 | 12/2011 | Gaw |
| 2012/0029410 A1 | 2/2012 | Koenig et al. |
| 2012/0061257 A1 | 3/2012 | Yu et al. |
| 2012/0078088 A1 | 3/2012 | Whitestone et al. |
| 2012/0083672 A1 | 4/2012 | Cui et al. |
| 2012/0150011 A1 | 6/2012 | Besio |
| 2012/0179006 A1 | 7/2012 | Jansen et al. |
| 2012/0190989 A1 | 7/2012 | Kaiser et al. |
| 2012/0271121 A1 | 10/2012 | Della Torre et al. |
| 2013/0041235 A1 | 2/2013 | Rogers et al. |
| 2013/0072870 A1 | 3/2013 | Heppe et al. |
| 2013/0121544 A1 | 5/2013 | Sarrafzadeh et al. |
| 2013/0123587 A1 | 5/2013 | Sarrafzadeh et al. |
| 2013/0137951 A1 | 5/2013 | Chuang et al. |
| 2013/0249695 A1 | 9/2013 | Hann et al. |
| 2013/0253285 A1 | 9/2013 | Bly et al. |
| 2013/0261496 A1 | 10/2013 | Engler et al. |
| 2013/0301255 A1 | 11/2013 | Kim et al. |
| 2013/0310440 A1 | 11/2013 | Duskin et al. |
| 2013/0333094 A1 | 12/2013 | Rogers et al. |
| 2013/0338661 A1 | 12/2013 | Behnke, II |
| 2014/0121479 A1 | 5/2014 | O'Connor et al. |
| 2014/0142984 A1 | 5/2014 | Wright et al. |
| 2014/0200486 A1 | 7/2014 | Bechtel et al. |
| 2014/0221792 A1 | 8/2014 | Miller et al. |
| 2014/0273025 A1 | 9/2014 | Hurskainen et al. |
| 2014/0275823 A1 | 9/2014 | Lane et al. |
| 2014/0288397 A1 | 9/2014 | Sarrafzadeh et al. |
| 2014/0298928 A1 | 10/2014 | Duesterhoft et al. |
| 2014/0316297 A1 | 10/2014 | McCaughan et al. |
| 2014/0318699 A1 | 10/2014 | Longinotti-Buitoni et al. |
| 2014/0365241 A1 | 12/2014 | Dillie et al. |
| 2015/0002168 A1 | 1/2015 | Kao et al. |
| 2015/0009168 A1 | 1/2015 | Levesque et al. |
| 2015/0094548 A1 | 4/2015 | Sabatini et al. |
| 2015/0157435 A1 | 6/2015 | Chasins et al. |
| 2015/0186607 A1 | 7/2015 | Gileijnse et al. |
| 2015/0216751 A1 | 8/2015 | Stokes et al. |
| 2015/0217518 A1 | 8/2015 | Chun et al. |
| 2015/0230863 A1 | 8/2015 | Youngquist et al. |
| 2015/0343173 A1 | 12/2015 | Tobescu et al. |
| 2015/0363567 A1 | 12/2015 | Pettus |
| 2015/0366499 A1 | 12/2015 | Sarrafzadeh et al. |
| 2015/0371522 A1 | 12/2015 | Mravyan et al. |
| 2016/0015962 A1 | 1/2016 | Shokoueinejad Maragheh et al. |
| 2016/0038055 A1 | 2/2016 | Wheeler et al. |
| 2016/0058342 A1 | 3/2016 | Maiz-Aguinaga et al. |
| 2016/0072308 A1 | 3/2016 | Nyberg et al. |
| 2016/0081580 A1 | 3/2016 | Bergelin et al. |
| 2016/0100790 A1 | 4/2016 | Cantu et al. |
| 2016/0101282 A1 | 4/2016 | Bergelin et al. |
| 2016/0113592 A1 | 4/2016 | Murugappan et al. |
| 2016/0166438 A1 | 6/2016 | Rovaniemi |
| 2016/0174631 A1 | 6/2016 | Tong et al. |
| 2016/0174871 A1 | 6/2016 | Sarrafzadeh et al. |
| 2016/0220172 A1 | 8/2016 | Sarrafzadeh et al. |
| 2016/0270672 A1 | 9/2016 | Chen et al. |
| 2016/0270968 A1 | 9/2016 | Stanford et al. |
| 2016/0278692 A1 | 9/2016 | Larson et al. |
| 2016/0296268 A1 | 10/2016 | Gee et al. |
| 2016/0310034 A1 | 10/2016 | Tonar et al. |
| 2016/0338591 A1* | 11/2016 | Lachenbruch ......... G16H 20/40 |
| 2016/0374588 A1 | 12/2016 | Shariff |
| 2017/0007153 A1 | 1/2017 | Tonar et al. |
| 2017/0014044 A1 | 1/2017 | Tonar et al. |
| 2017/0014045 A1 | 1/2017 | Tonar et al. |
| 2017/0105646 A1 | 4/2017 | Bryenton et al. |
| 2017/0124279 A1 | 5/2017 | Rothman |
| 2017/0156658 A1 | 6/2017 | Maharbiz et al. |
| 2017/0172489 A1 | 6/2017 | Afentakis |
| 2017/0172490 A1 | 6/2017 | Afentakis et al. |
| 2017/0188841 A1 | 7/2017 | Ma et al. |
| 2017/0238849 A1 | 8/2017 | Chapman et al. |
| 2017/0245799 A1 | 8/2017 | Fleischer et al. |
| 2017/0255812 A1 | 9/2017 | Kwon |
| 2017/0311807 A1 | 11/2017 | Fu et al. |
| 2017/0319066 A1 | 11/2017 | Ver Steeg |
| 2017/0319073 A1 | 11/2017 | DiMaio et al. |
| 2018/0020058 A1 | 1/2018 | Martines et al. |
| 2018/0045725 A1 | 2/2018 | Yoo et al. |
| 2018/0098735 A1 | 4/2018 | Cha |
| 2018/0220924 A1 | 8/2018 | Burns et al. |
| 2018/0220953 A1 | 8/2018 | Burns et al. |
| 2018/0220954 A1 | 8/2018 | Burns et al. |
| 2018/0220961 A1 | 8/2018 | Burns et al. |
| 2018/0360344 A1 | 12/2018 | Burns et al. |
| 2019/0000352 A1 | 1/2019 | Everett et al. |
| 2019/0038133 A1 | 2/2019 | Tran |
| 2019/0053751 A1 | 2/2019 | Torres |
| 2019/0060602 A1 | 2/2019 | Tran et al. |
| 2019/0069836 A1 | 3/2019 | Hettrick |
| 2019/0104981 A1 | 4/2019 | Sarrafzadeh et al. |
| 2019/0104982 A1 | 4/2019 | Dunn et al. |
| 2019/0117964 A1 | 4/2019 | Bahrami et al. |
| 2019/0134396 A1 | 5/2019 | Toth et al. |
| 2019/0142333 A1 | 5/2019 | Burns et al. |
| 2019/0147990 A1 | 5/2019 | Burns et al. |
| 2019/0148901 A1 | 5/2019 | Komoto |
| 2019/0150882 A1 | 5/2019 | Maharbiz et al. |
| 2019/0175098 A1 | 6/2019 | Burns et al. |
| 2019/0192066 A1 | 6/2019 | Schoess et al. |
| 2019/0246972 A1 | 8/2019 | Burns et al. |
| 2019/0269943 A1 | 9/2019 | Lewis, Jr. et al. |
| 2019/0282436 A1 | 9/2019 | Douglas et al. |
| 2019/0290189 A1 | 9/2019 | Sarrafzadeh et al. |
| 2019/0307360 A1 | 10/2019 | Tonar et al. |
| 2019/0307405 A1 | 10/2019 | Terry et al. |
| 2020/0008299 A1 | 1/2020 | Tran et al. |
| 2020/0043607 A1 | 2/2020 | Zerhusen et al. |
| 2020/0069240 A1 | 3/2020 | Burns |
| 2020/0069241 A1 | 3/2020 | Burns |
| 2020/0069242 A1 | 3/2020 | Burns et al. |
| 2020/0077892 A1 | 3/2020 | Tran |
| 2020/0078499 A1 | 3/2020 | Gadde et al. |
| 2020/0093395 A1 | 3/2020 | Tonar et al. |
| 2020/0100723 A1 | 4/2020 | Burns |
| 2020/0113488 A1 | 4/2020 | Al-Ali et al. |
| 2020/0127398 A1 | 4/2020 | Burns et al. |
| 2020/0296821 A1 | 9/2020 | Trublowski et al. |
| 2020/0297244 A1 | 9/2020 | Brownhill et al. |
| 2020/0297255 A1 | 9/2020 | Martinez et al. |
| 2021/0052427 A1 | 2/2021 | Awiszus et al. |
| 2021/0076974 A1 | 3/2021 | Burns |
| 2021/0159621 A1 | 5/2021 | Burns et al. |
| 2021/0204864 A1 | 7/2021 | Burns et al. |

(56) References Cited

U.S. PATENT DOCUMENTS

| | | |
|---|---|---|
| 2021/0290989 A1 | 9/2021 | Hall et al. |
| 2021/0307635 A1 | 10/2021 | Burns |
| 2022/0071555 A1 | 3/2022 | Burns et al. |
| 2022/0192587 A1 | 6/2022 | Burns et al. |
| 2022/0211291 A1 | 7/2022 | Tonar et al. |
| 2022/0211937 A1 | 7/2022 | Kamen et al. |
| 2022/0240840 A1 | 8/2022 | Burns |
| 2022/0273238 A1 | 9/2022 | Burns et al. |
| 2022/0285865 A1 | 9/2022 | Burns et al. |
| 2022/0287584 A1 | 9/2022 | Burns et al. |
| 2022/0330847 A1 | 10/2022 | Burns et al. |
| 2022/0409086 A1 | 12/2022 | Burns |
| 2023/0068683 A1 | 3/2023 | Burns et al. |
| 2023/0109698 A1 | 4/2023 | Tonar et al. |
| 2023/0148893 A1 | 5/2023 | Burns et al. |
| 2023/0240592 A1 | 8/2023 | Burns et al. |
| 2023/0329629 A1 | 10/2023 | Burns et al. |
| 2023/0335929 A1 | 10/2023 | Burns et al. |
| 2023/0337966 A1 | 10/2023 | Sarrafzadeh et al. |
| 2023/0346240 A1 | 11/2023 | Tonar et al. |
| 2023/0363698 A9 | 11/2023 | Burns |
| 2024/0039192 A1 | 2/2024 | Burns et al. |
| 2024/0081727 A1 | 3/2024 | Burns |
| 2024/0138696 A1 | 5/2024 | Burns et al. |
| 2024/0268753 A1 | 8/2024 | Burns et al. |
| 2024/0278013 A1 | 8/2024 | Samant |
| 2024/0389932 A1 | 11/2024 | Burns et al. |
| 2025/0023263 A1 | 1/2025 | Burns et al. |
| 2025/0049342 A1 | 2/2025 | Burns et al. |

FOREIGN PATENT DOCUMENTS

| | | |
|---|---|---|
| CA | 2609842 C | 10/2016 |
| CN | 102033166 A | 4/2011 |
| CN | 204119175 U | 1/2015 |
| CN | 104352230 A | 2/2015 |
| CN | 104567657 A | 4/2015 |
| CN | 104644125 A | 5/2015 |
| CN | 105578333 A | 5/2016 |
| CN | 105963074 A | 9/2016 |
| CN | 208111467 U | 11/2018 |
| DE | 102012011212 A1 | 12/2012 |
| EP | 0970656 A1 | 1/2000 |
| EP | 1080687 A1 | 3/2001 |
| EP | 1372475 B1 | 1/2004 |
| EP | 1569553 A1 | 9/2005 |
| EP | 3092946 A1 | 11/2016 |
| EP | 3280488 B1 | 12/2018 |
| GB | 2148513 | 5/1985 |
| GB | 2584808 A | 12/2020 |
| JP | H06-502323 | 3/1994 |
| JP | H10-201726 | 8/1998 |
| JP | 2000-060805 A | 2/2000 |
| JP | 2001-178705 | 7/2001 |
| JP | 2001-326773 A | 11/2001 |
| JP | 2003-169787 A | 6/2003 |
| JP | 2003-169788 A | 6/2003 |
| JP | 2003-202312 | 7/2003 |
| JP | 2003-290166 A | 10/2003 |
| JP | 2005-52227 | 3/2005 |
| JP | 2009-268611 A | 11/2009 |
| JP | 4418419 | 2/2010 |
| JP | 2013-198639 A | 10/2013 |
| JP | 2015-134074 | 7/2015 |
| JP | 2015-529482 | 10/2015 |
| KR | 10-2014-0058445 | 5/2014 |
| WO | 1996/010951 A1 | 4/1996 |
| WO | 2001/054580 A1 | 8/2001 |
| WO | 2002/080770 A1 | 10/2002 |
| WO | 2004/105602 A1 | 12/2004 |
| WO | 2005/099644 A2 | 10/2005 |
| WO | 2006/029035 A1 | 3/2006 |
| WO | 2007/098762 A1 | 9/2007 |
| WO | 2009/144615 A1 | 12/2009 |
| WO | 2010/060102 A2 | 5/2010 |
| WO | 2011/004165 A1 | 1/2011 |
| WO | 2011/022418 A2 | 2/2011 |
| WO | 2011/048556 A2 | 4/2011 |
| WO | 2011/080080 A1 | 7/2011 |
| WO | 2011/080262 A1 | 7/2011 |
| WO | 2011/084722 A1 | 7/2011 |
| WO | 2011/091517 A1 | 8/2011 |
| WO | 2011/143071 A2 | 11/2011 |
| WO | 2013/033724 A1 | 3/2013 |
| WO | 2013/114356 A1 | 8/2013 |
| WO | 2013/116242 A2 | 8/2013 |
| WO | 2013/140714 A1 | 9/2013 |
| WO | 2014/147515 A1 | 9/2014 |
| WO | 2014/186894 A1 | 11/2014 |
| WO | 2015/003015 A2 | 1/2015 |
| WO | 2015/022583 A2 | 2/2015 |
| WO | 2015/077838 A1 | 6/2015 |
| WO | 2015/168720 A1 | 11/2015 |
| WO | 2015/169911 A1 | 11/2015 |
| WO | 2015/195720 A1 | 12/2015 |
| WO | 2016/098062 A1 | 6/2016 |
| WO | 2016/172263 A1 | 10/2016 |
| WO | 2016/172264 A1 | 10/2016 |
| WO | 2017/032393 | 3/2017 |
| WO | 2017/214188 A1 | 12/2017 |
| WO | 2017/218818 A2 | 12/2017 |
| WO | 2018/071715 A1 | 4/2018 |
| WO | 2018/077560 A1 | 5/2018 |
| WO | 2018/115461 A1 | 6/2018 |
| WO | 2018/144938 | 8/2018 |
| WO | 2018/144941 | 8/2018 |
| WO | 2018/144943 | 8/2018 |
| WO | 2018/144946 | 8/2018 |
| WO | 2018/168424 A1 | 9/2018 |
| WO | 2018/189265 A1 | 10/2018 |
| WO | 2018/209100 A1 | 11/2018 |
| WO | 2018/234443 A1 | 12/2018 |
| WO | 2018/236739 | 12/2018 |
| WO | 2019/020551 A1 | 1/2019 |
| WO | 2019/030384 A2 | 2/2019 |
| WO | 2019/048624 A1 | 3/2019 |
| WO | 2019/048626 A1 | 3/2019 |
| WO | 2019/048638 A1 | 3/2019 |
| WO | 2019/072531 A1 | 4/2019 |
| WO | 2019/073389 A1 | 4/2019 |
| WO | 2019/076967 A2 | 4/2019 |
| WO | 2019/096828 A1 | 5/2019 |
| WO | 2019/099810 A1 | 5/2019 |
| WO | 2019/099812 A1 | 5/2019 |
| WO | 2019/113481 | 6/2019 |
| WO | 2019/157290 | 8/2019 |
| WO | 2019/162272 A1 | 8/2019 |
| WO | 2020/014779 A1 | 1/2020 |
| WO | 2020/043806 A1 | 3/2020 |
| WO | 2020/053290 A1 | 3/2020 |
| WO | 2020/077100 A1 | 4/2020 |
| WO | 2020/118256 A1 | 6/2020 |
| WO | 2020/187643 A1 | 9/2020 |
| WO | 2020/187851 A1 | 9/2020 |
| WO | 2020/234429 A2 | 11/2020 |

OTHER PUBLICATIONS

Alanen, "Measurement of Hydration in the Stratum Corneum with the MoistureMeter and Comparison with the Corneometer," *Skin Research and Technology*, 10:32-37 (2004).

Alberts et al., "The Extracellular Matrix of Animals," *Molecular Biology of the Cell*, 4th ed., pp. 1065-1127 (2002).

Allman et al., "Pressure Ulcer Risk Factors Among Hospitalized Patients with Activity Limitation," *JAMA*, 273:865-870 (1995).

Anonymous, "Recommended Practices for Positioning the Patient in the Perioperative Practice Setting," in *Perioperative Standards, Recommended Practices, and Guidelines*, AORN, Inc., 525-548 (2006).

Arao et al., "Morphological Characteristics of the Dermal Papillae in the Development of Pressure Sores," *World Wide Wounds* (Mar. 1999), 6 pages (obtained online).

(56)                   References Cited

OTHER PUBLICATIONS

Arimoto et al., "Non-Contact Skin Moisture Measurement Based on Near-Infrared Spectroscopy," *Applied Spectroscopy*, 58(12):1439-1446 (2004).

Avci et al., "Low-Level Laser (Light) Therapy (LLLT) in Skin: Stimulating, Healing, Restoring," *Seminars in Cutaneous Medicine and Surgery*, 32(1)41-52 (Mar. 2013).

Australian Intellectual Property Office, Office Action issued on May 1, 2014, for corresponding Australian patent application No. 2011253253 (pp. 1-10) and pending claims (pp. 11-15) pp. 1-15.

Australian Patent Office, Office Action issued on Jun. 1, 2015, for corresponding Australian Patent Application No. 2011253253 (pp. 1-4) and claims (pp. 5-10) pp. 1-10.

Bader et al., "Effect of Externally Applied Skin Surface Forces on Tissue Vasculature," *Archives of Physical Medicine and Rehabilitation*, 67(11):807-11 (1986).

Barnes, "Moisture Meters for Use on Thin Lumber and Veneers," *Moisture Register Co.*, 1-5 (1956).

Bates-Jensen et al., "Subepidermal Moisture Predicts Erythema and Stage 1 Pressure Ulcers in Nursing Home Residents: A Pilot Study," *Journal of the American Geriatric Society*, 55:1199-1205 (2007).

Bates-Jensen et al., "Subepidermal moisture differentiates erythema and stage 1 pressure ulcers in nursing home residents," *Wound Repair Regeneration*, 16:189-197 (2008).

Bates-Jensen et al., "Subepidermal Moisture Is Associated with Early Pressure Ulcer Damage in Nursing Home Residents with Dark Skin Tones; Pilot Findings," *Journal of Wound Ostomy and Continence Nursing*, 36(3):277-284 (2009).

Bates-Jensen et al., "Subepidermal Moisture Detection of Pressure Induced Tissue Damage on the Trunk: The Pressure Ulcer Detection Study Outcomes," *Wound Repair and Regeneration*, 25:502-511 (2017).

Berggren, "Capacitive Biosensors," Electroanalysis, 13(3):173-180 (2001), Wiley-VCH (publisher), Weinheim, Germany.

Bergstrand et al., "Pressure-induced Vasodilation and Reactive Hyperemia at Different Depths in Sacral Tissue Under Clinically Relevant Conditions," *Microcirculation*, 21:761-771 (2014).

Bergstrom et al., "Pressure Ulcers in Adults: Prediction and Prevention," Clinical Practice Guideline—Quick Reference Guide for Clinicians, 117 (1992).

Black et al., "Differential Diagnosis of Suspected Deep Tissue Injury," *International Wound Journal*, 13(4):531-539 (2015).

Brem et al., "Protocol for the Successful Treatment of Pressure Ulcers," *The American Journal of Surgery*, 188 (Suppl. To Jul. 2004):9S-17S (2004).

Brem et al., "High cost of stage IV pressure ulcers," American Journal of Surgery, 200:473-477 (2010).

Brienza et al., "Friction-Induced Skin Injuries—Are They Pressure Ulcers?," *Journal of Wound Ostomy and Continence Nursing*, 42(1):62-64 (2015).

Brunetti et al., "Validation of a sub-epidermal moisture scanner for early detection of pressure ulcers in an ex vivo porcine model of localized oedema," *J. Tissue Viability*, 32(4):508-515 (available online Jul. 8, 2023).

Byrne et al., "Sub epidermal moisture measurement and targeted SSKIN bundle interventions, a winning combination for the treatment of early pressure ulcer development," *Int. Wound J.*, 2022:1-13 (published online Nov. 25, 2022).

Carmo-Araujo et al., "Ischaemia and reperfusion effects on skeletal muscle tissue: morphological and histochemical studies," *International Journal of Experimental Pathology*, 88:147-154 (2007).

Ceelen et al., "Compression-induced damage and internal tissue strains are related," *Journal of Biomechanics*, 41:3399-3404 (2008).

Chan et al., "Using Wireless Measuring Devices and Tablet PC to Improve the Efficiency of Vital Signs Data Collection in Hospital," 4 pp., 2014 IEEE International Symposium on Bioelectronics and Bioinformatics (IEEE ISBB 2014).

Ching et al., "Tissue electrical properties monitoring for the prevention of pressure sore," *Prosthetics and Orthotics International*, 35(4):386-394 (2011).

Clendenin et al., "Inter-operator and inter-device agreement and reliability of the SEM Scanner," *Journal of Tissue Viability*, 24(1):17-23 (2015).

De Lorenzo et al., "Predicting body cell mass with bioimpedance by using theoretical methods: a technological review," *Journal of Applied Physiology*, 82(5):1542-1558 (1997).

De Oliveira et al., "Sub-epidermal moisture versus tradition and visual skin assessments to assess pressure ulcer risk in surgery patients," *Journal of Wound Care*, 31(3):254-264 (2022), Mark Allen Group (pub.) (obtained online).

Demarre et al., "The cost of pressure ulcer prevention and treatment in hospitals and nursing homes in Flanders: A cost-of-illness study," *International Journal of Nursing Studies*, 1-14 (2015).

Dodde et al., "Bioimpedance of soft tissue under compression," *Physiology Measurement*, 33(6):1095-1109 (2012).

Dupont, "Pyralux® FR Coverlay, Bondply & Sheet Adhesive," webpage, Retrieved from: www2.dupont.com/Pyralux/en_US/products/adhesives_films/FR/FR_films_html pp. 1-2 (2012).

DuPont, "General Specifications for Kapton Polyimide Film," Retrieved from Dupont: http://www2.dupont.com/Kapton/en_US/assets/downloads/pdf/Gen_Specs.pdf, pp. 1-7 (2012).

DuPont, "Pyralux® FR Copper-clad Laminate," webpage, Retrieved from: www2.dupont.com/Pyraluxlen_US/ productsllaminate/FR/pyralux_fr.html, pp. 1-2 (2012).

Eberlein-Gonska et al., "The Incidence and Determinants of Decubitus Ulcers in Hospital Care: An Analysis of Routine Quality Management Data at a University Hospital," *Deutsches Arzteblatt International*, 110(33-34):550-556 (2013).

European Patent Office, ESSR issued on Aug. 22, 2014, for corresponding European Patent Application No. 11781061.4 (pp. 1-7) and pending claims (pp. 3-10) pp. 1-10.

European Patent Office, Office Action issued on Jul. 13, 2015, for corresponding European Patent Application No. 11781061.4 (pp. 1-5) and claims (pp. 6-9) pp. 1-9.

Extended European Search Report mailed Aug. 30, 2016, in European Application No. 16169670.

Extended European Search Report mailed Oct. 18, 2016, in European Patent Application No. 16166483.4.

Extended European Search Report dated Mar. 13, 2017, in European Patent Application No. 16196899.5.

Extended European Search Report mailed Oct. 25, 2019, in European Patent Application No. 19186393.5.

Extended European Search Report mailed Nov. 19, 2019, in European Patent Application No. 19190000.0.

Extended European Search Report mailed Feb. 6, 2020, in European Patent Application No. 18748733.5.

Extended European Search Report mailed Feb. 10, 2020, in European Patent Application No. 18748025.6.

Extended European Search Report mailed Feb. 10, 2020, in European Patent Application No. 18748512.3.

Extended European Search Report mailed Jun. 24, 2020, in European Patent Application No. 18747707.0.

Extended European Search Report dated Mar. 17, 2022, in European Patent Application No. 19838240.0.

Extended European Search Report dated May 24, 2022, in European Patent Application No. 19871332.3.

Extended European Search Report dated Feb. 1, 2023, in European Application No. 22211200.

Extended European Search Report completed Nov. 7, 2023, in European Patent Application No. 23188775.3.

Extended European Search Report dated Jun. 11, 2024, in European Patent Application No. 24158801.1.

Ford, "Hospice Wins Award for Innovation in Pressure Ulcer Prevention," *Nursing Times*, downloaded and printed on Apr. 18, 2020, from https://www.nursingtimes.net/news/research-and-innovation/hospice-wins-award-for-innovation-in-pressure-ulcer-prevention-30-11-2018/ (2018).

Gabriel et al., "The dielectric properties of biological tissues: II. Measurements in the frequency range 10 Hz to 20 GHZ," *Physics in Medicine and Biology*, 41:2251-69 (1996).

Gabriel, "Compilation of the Dielectric Properties of Body Tissues at Rf and Microwave Frequencies Report," Occupational and Environmental Health Directorate, (1996).

(56) References Cited

OTHER PUBLICATIONS

Gardiner et al., "Incidence of hospital-acquired pressure ulcers—a population-based cohort study," *International Wound Journal*, 11(6):696-700 (2014).

Gershon et al., "SEM Scanner Readings to Assess Pressure Induced Tissue Damage," Proceedings of the 17th Annual European Pressure Ulcer Advisory Panel (EPUAP) meeting, Stockholm, Sweden (2014).

Gonzalez-Correa et al., "Electrical bioimpedance readings increase with higher pressure applied to the measuring probe," *Physiology Measurement*, 26:S39-S47 (2005).

Great Britain Search Report dated Apr. 27, 2020, in Great Britain Patent Application No. GB2002889.0.

Great Britain Search Report dated Jun. 28, 2021, in Great Britain Patent Application No. GB2106848.1.

Great Britain Search Report dated Feb. 9, 2022, in Great Britain Patent Application No. GB2118088.0.

Great Britain Search Report dated Feb. 14, 2022, in Great Britain Patent Application No. GB2118092.2.

Guihan et al., "Assessing the feasibility of subepidermal moisture to predict erythema and stage 1 pressure ulcers in persons with spinal cord injury: A pilot study," *Journal of Spinal Cord Medicine*, 35(1):46-52 (2012).

Hamazoto et al., "Estimate of Burn Depth by Non-Invasive Capacitance Measurement," *Japan Soc. ME & BE*, 42:266 (Jun. 2003).

Harrow, "Subepidermal moisture surrounding pressure ulcers in persons with a spinal cord injury: A pilot study," *Journal of Spinal Cord Medicine*, 37(6):719-728 (2014).

Hou, "Section IV. Osteofascial Compartment Syndrome," *Limbs Trauma*, 7:215-217 (2016), Hubei Science & Technology Publishing House (pub.), Wuhan, China.

Houwing et al., "Pressure-induced skin lesions in pigs: reperfusion injury and the effects of vitamin E," *Journal of Wound Care*, 9(1):36-40 (2000).

Huang et al., "A device for skin moisture and environment humidity detection," Sensors and Actuators B: Chemical, 206-212 (2008).

International Search Report and Written Opinion mailed Feb. 9, 2012, for International Patent Application No. PCT/US2011/035618.

International Search Report and Written Opinion mailed Jul. 22, 2016, for International Patent Application No. PCT/US2016/28515.

International Search Report and Written Opinion mailed Jul. 26, 2016, for International Patent Application No. PCT/US2016/28516.

International Search Report mailed Apr. 12, 2018, issued in International Patent Application No. PCT/US2018/016731.

International Search Report mailed Apr. 12, 2018, issued in International Patent Application No. PCT/US2018/016738.

International Search Report mailed Apr. 26, 2018, issued in International Patent Application No. PCT/US2018/016741.

International Search Report mailed Jul. 12, 2018, issued in International Patent Application No. PCT/US2018/016736.

International Search Report mailed Sep. 10, 2018, issued in International Patent Application No. PCT/US2018/038055.

International Search Report mailed Jan. 29, 2019, issued in International Patent Application No. PCT/US2018/061494.

International Search Report mailed Feb. 5, 2019, issued in International Patent Application No. PCT/US2018/064527.

International Search Report mailed Feb. 11, 2019, issued in International Patent Application No. PCT/US2018/061497.

International Search Report mailed May 29, 2019, issued in International Patent Application No. PCT/US2019/017226.

International Search Report mailed Mar. 9, 2020, issued in International Patent Application No. PCT/US2019/055655.

International Search Report mailed Dec. 8, 2020, issued in International Patent Application PCT/US2020/051134.

International Search Report mailed Aug. 17, 2021, issued in International Patent Application PCT/US2021/023818.

International Search Report mailed May 13, 2022, issued in International Patent Application PCT/US2022/014913.

International Search Report mailed Aug. 2, 2022, issued in International Patent Application PCT/US2022/025508.

International Search Report mailed Aug. 15, 2022, issued in International Patent Application PCT/US2022/019338.

International Search Report mailed May 29, 2024, issued in International Patent Application PCT/US2023/074190.

Jan et al., "Local cooling reduces skin ischemia under surface pressure in rats: an assessment by wavelet analysis of laser Doppler blood flow oscillations," *Physiology Measurement*, 33(10):1733-1745 (2012).

Jaskowski, "Evaluation of the Healing Process of Skin Wounds by Means of Skin Absolute Value of Electrical Impedance," *Dermatol. Mon.schr.*, 172(4):223-228 (1986).

Jiang et al., "Ischemia-Reperfusion Injury-Induced Histological Changes Affecting Early Stage Pressure Ulcer Development in a Rat model," *Ostomy Wound Management*, 57:55-60 (2011).

Jiang et al., "Expression of cytokines, growth factors and apoptosis-related signal molecules in chronic pressure ulcer wounds healing," *Spinal Cord*, 52(2):145-151 (2014).

Jiricka et al., "Pressure Ulcer Risk factors in an ICU Population," *American Journal of Critical Care*, 4:361-367 (1995).

Kanai et al., "Electrical measurement of fluid distribution in legs and arms," *Medical Progress through Technology Journal*, 12:159-170 (1987).

Kasuya et al., "Potential application of in vivo imaging of impaired lymphatic duct to evaluate the severity of pressure ulcer in mouse model," *Scientific Reports*, 4:4173 (7 pages) (2014).

Lee, "CapSense Best Practices," Application Note 2394, 1-10 (2007).

Liu et al., "A Systematic Review of Electrical Stimulation for Pressure Ulcer Prevention and Treatment in People with Spinal Cord Injuries," *The Journal of Spinal Cord Medicine*, 37(6):703-718 (2014).

Loerakker et al., "Temporal Effects of Mechanical Loading on Deformation-Induced Damage in Skeletal Muscle Tissue," *Annual Review of Biomedical Engineering*, 38(8):2577-2587 (2010).

Loerakker et al., "The effects of deformation, ischemia, and reperfusion on the development of muscle damage during prolonged loading," *Journal of Applied Physiology*, 111(4):1168-1177 (2011).

Lustig et al., "A machine learning algorithm for early detection of heel deep tissue injuries based on a daily history of sub-epidermal moisture measurements," *Int. Wound J.*, 2021:1-10 (published online Dec. 1, 2021).

Lyder et al., "Quality of Care for Hospitalized Medicare Patients at Risk for Pressure Ulcers," *Archives of Internal Medicine*, 161:1549-1554 (2001).

Martinsen, "Bioimpedance and Bioelectricity Basics," Elsevier Academic Press, Chapters 1 and 10 (2015).

Mathiesen et al., "Are labour-intensive efforts to prevent pressure ulcers cost-effective?" *Journal of Medical Economics*, 16(10):1238-1245 (2013).

Matthie et al., "Analytic assessment of the various bioimpedance methods used to estimate body water," *Journal of Applied Physiology*, 84(5):1801-1816 (1998).

Miller et al., "Lymphatic Clearance during Compressive Loading," *Lymphology*, 14(4):161-166 (1981).

Moore et al., "A randomised controlled clinical trial of repositioning, using the 30° tilt, for the prevention of pressure ulcers," *Journal of Clinical Nursing*, 20:2633-2644 (2011).

Moore et al., "Pressure ulcer prevalence and prevention practices in care of the older person in the Republic of Ireland," *Journal of Clinical Nursing*, 21:362-371 (2012).

Moore et al., "A review of PU prevalence and incidence across Scandinavia, Iceland and Ireland (Part I)", *Journal of Wound Care*, 22(7):361-362, 364-368 (2013).

Moore et al., "Subepidermal Moisture (SEM) and Bioimpedance: A Literature Review of a Novel Method for Early Detection of Pressure-Induced Tissue Damage (Pressure Ulcers)," *International Wound Journal*, 14(2):331-337 (2016).

Moore, "Using SEM (Sub Epidermal Moisture) Measurement for Early Pressure Ulcer Detection," Institute for Pressure Injury Prevention, WCICT 2017 (Jun. 20-21), Manchester, UK, 7 pp., avail-

(56) References Cited

OTHER PUBLICATIONS able at www.pressureinjuryprevention.com/wp-content/uploads/2017/07/ipip_Moore_Sub_Epidermal_Moisture_notes.pdf(2017) (obtained online).

Moore et al., "SEM Scanner Made Easy," *Wounds International*, pp. 1-6, available at www.woundsinternational.com (2018).

Mulasi, "Bioimpedance at the Bedside: Current Applications, Limitations, and Opportunities," *Nutritional Clinical Practice*, 30(2):180-193 (2015).

Musa et al., "Clinical impact of a sub-epidermal moisture scanner: what is the real-world use?," *J. Wound Care*, 30(3):2-11 (2021), Mark Allen Group (pub.) (obtained online).

National Pressure Ulcer Advisory Panel et al., "Prevention and Treatment of Pressure Ulcers: Clinical Practice Guideline," Cambridge Media, (2014).

Nixon et al., "Pathology, diagnosis, and classification of pressure ulcers: comparing clinical and imaging techniques," *Wound Repair and Regeneration*, 13(4):365-372 (2005).

Nuutinen et al., "Validation of a new dielectric device to assess changes of tissue water in skin and subcutaneous fat," *Physiological Measurement*, 25:447-454 (2004).

O'Goshi, "Skin conductance; validation of Skicon-200EX compared to the original model, Skicon-100," *Skin Research and Technology*, 13:13-18 (2007).

Oliveira, "The Accuracy of Ultrasound, Thermography, Photography and Sub-Epidermal Moisture as a Predictor of Pressure Ulcer Presence—a Systematic Review," RCSI, School of Nursing thesis (2015).

Oomens et al., "Pressure Induced Deep Tissue Injury Explained," *Annual Review of Biomedical Engineering*, 43(2):297-305 (2015).

Pang et al. (eds.) *Diagnosis and Treatment of Diabetes*, China Press of Traditional Chinese Medicine (publisher), Beijing, China, pp. 466-468 (Oct. 2016), with English Translation.

Partial European Search Report dated Sep. 6, 2023, in European Application No. 23188775.3.

Partial European Search Report completed Mar. 27, 2024, in European Patent Application No. 23208591.0.

Partial European Search Report completed Apr. 16, 2024, in European Patent Application No. 24151800.0.

Ross et al., "Assessment of Sub-Epidermal Moisture by Direct Measurement of Tissue Biocapacitance," *Medical Engineering & Physics*, 73:92-99 (Jul. 26, 2019).

Rotaru et al., "Friction between Human Skin and Medical Textiles for Decubitus Prevention," *Tribology International*, 65:91-96 (2013).

Saxena, *The Pocket Doctor: Obstetrics & Gynecology*, pp. 76-77 (2017), Tianjin Science & Technology Translation & Publishing Co. Ltd. (pub.), Tianjin, China.

Scallan et al., "Chapter 4: Pathophysiology of Edema Formation," *Capillary Fluid Exchange: Regulation, Functions, and Pathology*, 47-61 (2010).

Schultz et al., "Extracellular matrix: review of its role in acute and chronic wounds," World Wide Wounds, 1-20 (2005).

Schwan, "Electrical properties of tissues and cells," *Advances in Biology and Medical Physics*, 15:148-199 (1957).

Seibert et al., "Technical Expert Panel Summary Report: Refinement of a Cross-Setting Pressure Ulcer/Injury Quality Measure for Skilled Nursing Facilities, Inpatient Rehabilitation Facilities, Long-Term Care Hospitals, and Home Health Agencies," RTI International Abt Associates, CMS Contract No. HHSM-500-2013-130151, 49 pp. (Aug. 2019).

Sener et al., "Pressure ulcer-induced oxidative organ injury is ameliorated by beta-glucan treatment in rats," *International Immunopharmacology*, 6(5):724-732 (2006).

Sewchuck et al., "Prevention and Early Detection of Pressure Ulcers in Patients Undergoing Cardiac Surgery," *AORN Journal*, 84(1):75-96 (2006).

Sprigle et al., "Analysis of Localized Erythema Using Clinical Indicators and Spectroscopy," *Ostomy Wound Management*, 49:42-52 (2003).

Stekelenburg et al., "Role of ischemia and deformation in the onset of compression-induced deep tissue injury: MRI-based studies in a rat model," *Journal of Applied Physiology*, 102:2002-2011 (2007).

Stekelenburg et al., "Deep Tissue Injury: How Deep is Our Understanding?" *Archives of Physical Medicine Rehabilitation*, 89(7):1410-1413 (2008).

Supplementary Partial European Search Report dated Jan. 27, 2020, in European Application No. 18747707.

Supplementary European Search Report dated Jul. 13, 2021, in European Application No. 18887039.

Supplementary European Search Report dated Oct. 1, 2021, in European Application No. 19751130.

Supplementary Partial European Search Report completed Jan. 10, 2024, in European Application No. 21782145.

Supplementary European Search Report completed May 8, 2024, in European Application No. 21782145.

Swisher et al., "Impedance sensing device enables early detection of pressure ulcers in vivo," *Nature Communications*, 6:6575-6584 (2015).

Thomas et al., "Hospital-Acquired Pressure Ulcers and Risk of Death," *Journal of the American Geriatrics Society*, 44:1435-1440 (1996).

Thomas, "Prevention and Treatment of Pressure Ulcers," *J. Am. Med. Dir. Assoc.*, 7:46-59 (2006).

Truong et al., "Pressure Ulcer Prevention in the Hospital Setting Using Silicone Foam Dressings," *Cureus*, 8(8):e730, pp. 1-6 (2016).

Tur et al., "Topical Hydrogen Peroxide Treatment of Ischemic Ulcers in the Guinea Pig: Blood Recruitment in Multiple Skin Sites," *J. Am. Acad. Dermatol.*, 33:217-221 (1995).

Valentinuzzi et al., "Bioelectrical Impedance Techniques in Medicine. Part II: Monitoring of Physiological Events by Impedance," *Critical Reviews in Biomedical Engineering*, 24(4-6):353-466 (1996).

Vangilder et al., "Results of Nine International Pressure Ulcer Prevalence Surveys: 1989 to 2005," *Ostomy Wound Management*, 54(2):40-54 (2008).

Visscher et al., "Face Masks for Noninvasive Ventilation: Fit, Excess Skin Hydration, and Pressure Ulcers," *Respiratory Care*, 60(11):1536-1547 (Nov. 2015).

Vowden et al., "Diabetic Foot Ulcer or Pressure Ulcer? That Is the Question," *The Diabetic Foot Journal*, 18:62-66 (2015).

Wagner et al., "Bioelectrical Impedance as a Discriminator of Pressure Ulcer Risk," *Advances in Wound Care*, 9(2):30-37 (1996).

Wang et al., "A Wireless Biomedical Instrument for Evidence-Based Tissue Wound Characterization," *Wireless Health*, pp. 222-223 (2010).

Wang, "Biomedical System for Monitoring Pressure Ulcer Development," UCLA Electronic Theses and Dissertations, California, USA, pp. 1-123 (Dec. 31, 2013).

Watanabe et al., "CT analysis of the use of the electrical impedance technique to estimate local oedema in the extremities in patients with lymphatic obstruction," *Medical and Biological Engineering and Computing*, 36(1):60-65 (1998).

Weber et al., "Remote Wound Monitoring of Chronic Ulcers," IEEE Transactions on Information Technology in Biomedicine, IEEE Service Center, Los Alamitos, CA, vol. 13(2):371-377 (Mar. 1, 2010).

Weiss, "Tissue destruction by neutrophils," *The New England Journal of Medicine*, 320(6):365-76 (1989).

Yang, *Handbook of Practical Burn Surgery*, p. 48 (2008), People's Military Medical Press (pub.), Beijing, China.

Zanibbi, "Pattern Recognition: An Overview," downloaded from https://www.cs.rit.edu/~rlaz/prec20092/slides/Overview.pdf, 30 pp. (2010).

Bluestein et al., "Pressure Ulcers: Prevention, Evaluation, and Management," *Am. Fam. Physician*, 78(10):1186-1194 (Nov. 15, 2008).

De Oliveira et al., "The accuracy of ultrasound, thermography, photography and sub-epidermal moisture as a predictor of pressure ulcer presence—a systematic review," unsigned thesis submitted to the School of Postgraduate Studies, Faculty of Medicine and Health Sciences, Royal College of Surgeons in Ireland, 316 pp. (2015),

(56)        References Cited

OTHER PUBLICATIONS retrieved from http://pstorage-rcsi-9048708668.s3.amazonaws.com/19329779/Theaccuracyofultrasoundthermographyphotographyandsubepi.pdf.
Extended European Search Report completed Jan. 1, 2025, in European Patent Application No. 22767802.6.
Extended European Search Report completed Jan. 3, 2025, in European Patent Application No. 24214401.2.
Extended European Search Report completed Feb. 3, 2025, in European Patent Application No. 24214403.8.
Great Britain Search Report dated Oct. 21, 2024, in Great Britain Patent Application No. GB2411677.4.
National Institute for Health and Care Excellence ("NICE"), "Pressure Ulcers: Prevention and Management," *Clinical Guideline*, 11 pp. (Apr. 23, 2014).
Partial European Search Report completed May 16, 2025, in European Application No. 25154882.
Reid et al., "Pressure Ulcer Prevention and Treatment: Use of Prophylactic Dressings," *Chronic Wound Care Management and Research*, 3:117-121 (Oct. 11, 2016).

Stekelenburg et al., "Compression-Induced Tissue Damage: Animal Models," in *Pressure Ulcer Research*, Springer-Verlag, Berlin/Heidelberg, pp. 187-204 (Jan. 1, 2005).
Vapiwala et al., "Enhancing Career Paths for Tomorrow's Radiation Oncologists," *International Journal of Radiation: Oncology Biology Physics*, 105(1):52-63 (May 22, 2019) (Pergamon Press).
Episcan I-200 marketing information, obtained from Longport Inc. website at longportinc.com/episcan-i-200, copyright 2016 (printed Dec. 2025).
Extended European Search Report completed Sep. 30, 2025, in European Application No. 25181955.
National Pressure Ulcer Advisory Panel et al., "Prevention and Treatment of Pressure Ulcers: Quick Reference Guide," Cambridge Media, available at https://www.nzwcs.org.nz/images/International_PUG/Quick_Reference_Guide_DIGITAL-PPPIA-Jan2016.pdf (2014).
Partial European Search Report completed May 27, 2025, in European Application No. 24200505.
Quintavalle et al., "Use of High-Resolution, High-Frequency Diagnostic Ultrasound to Investigate the Pathogenesis of Pressure Ulcer Development," *Advances in Skin & Wound Care*, 19(9):498-505 (Nov./Dec. 2006).

* cited by examiner

HEALTHY TISSUE

INTERCELLULAR SPACE & RUPTURED CELLS (FREE WATER)

FLUID

BONE

COMPRESSED DAMAGED TISSUE EXPELS FLUID (REDUCING MOISTURE IN TISSUE) AND FIELD PENETRATES INTO BONE

SEM TREND ANALYSIS

CROSS REFERENCE TO RELATED APPLICATIONS

This application is a continuation of U.S. patent application Ser. No. 16/213,664 filed Dec. 7, 2018, which claims the benefit of U.S. provisional patent application Ser. Nos. 62/596,089 filed on Dec. 7, 2017, and 62/623,857 filed on Jan. 30, 2018, each of which are incorporated by reference in their entireties herein.

FIELD

The present disclosure provides methods and apparatus for detecting tissue damage through evaluation of trends in Sub-epidermal Moisture (SEM) values.

BACKGROUND

The skin is the largest organ in the human body. It is readily exposed to different kinds of damages and injuries. When the skin and its surrounding tissues are unable to redistribute external pressure and mechanical forces, ulcers may be formed. Prolonged continuous exposure to even modest pressure, such as the pressure created by the body weight of a supine patient on their posterior skin surfaces, may lead to a pressure ulcer.

SUMMARY

In an aspect, the present disclosure provides for, and includes, a method of detecting tissue damage before it is visible on a patient's skin, comprising: measuring a plurality of sub-epidermal moisture (SEM) values at a single location at incremental times, calculating a slope between the latest SEM value and the immediately prior SEM value, comparing this slope to a threshold value, and determining that there is tissue damage if the slope exceeds the threshold value.

In an aspect, the present disclosure provides for, and includes, a method of detecting tissue damage before it is visible on a patient's skin, comprising: measuring a plurality sub-epidermal moisture (SEM) values at a plurality of locations at incremental times, calculating a delta value for the plurality of SEM values for each time, calculating a slope between the latest delta value and the immediately prior delta value, comparing this slope to a threshold value, and determining that there is tissue damage if the slope exceeds the threshold value.

In an aspect, the present disclosure provides for, and includes, a method of detecting tissue damage before it is visible on a patient's skin, comprising: measuring a plurality of sub-epidermal moisture (SEM) values at a single location at each of a plurality of incremental times, calculating a SEM delta value for each incremental time, fitting a curve to a predetermined number of the most-recent SEM delta values, calculating a curvature of the fitted curve, comparing this curvature to a threshold value, and determining that there is tissue damage if the curvature exceeds the threshold value.

BRIEF DESCRIPTION OF THE DRAWINGS

Aspects of the disclosure are herein described, by way of example only, with reference to the accompanying drawings. With specific reference now to the drawings in detail, it is stressed that the particulars shown are by way of example and are for purposes of illustrative discussion of aspects of the disclosure. In this regard, the description and the drawings, considered alone and together, make apparent to those skilled in the art how aspects of the disclosure may be practiced.

DETAILED DESCRIPTION

Figures 1A, 1B, 1C:
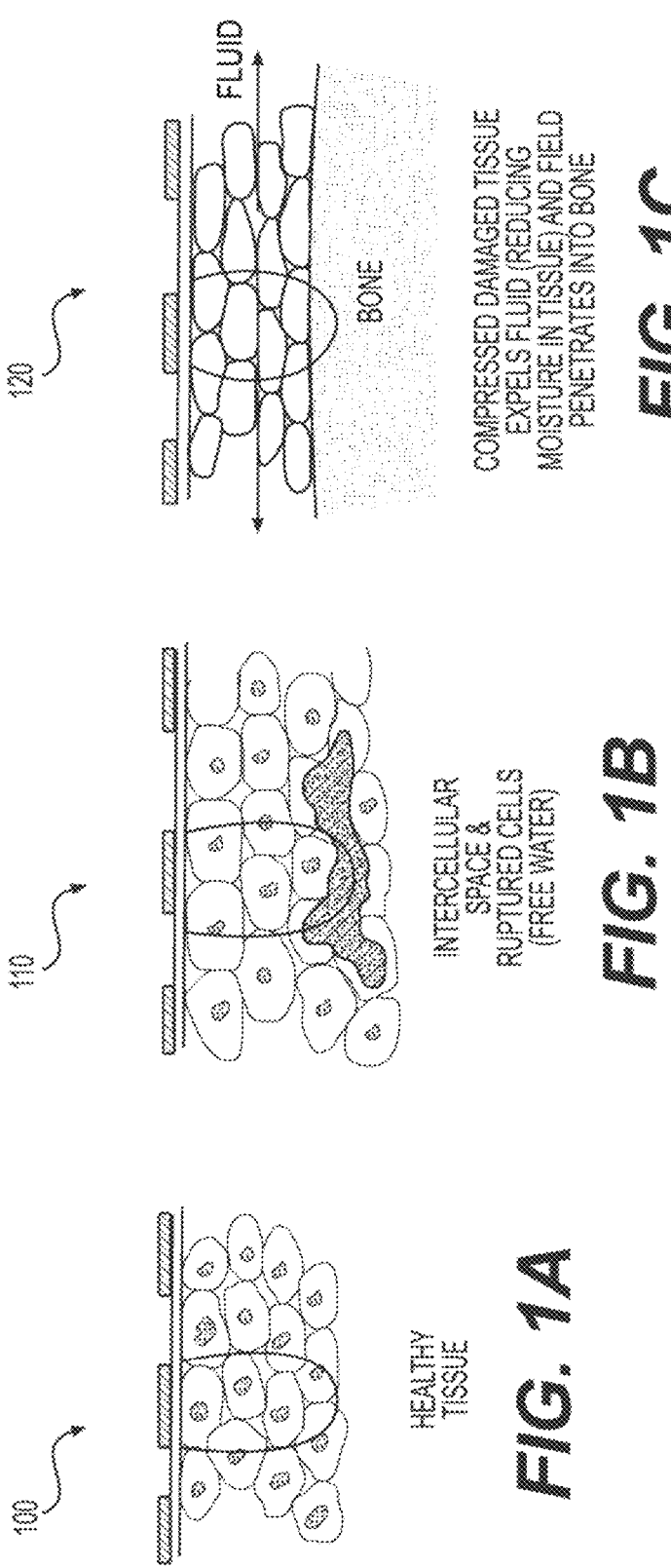
FIGS. 1A, 1B, and 1C illustrate a progression of tissue damage toward a pressure ulcer.

This description is not intended to be a detailed catalog of all the different ways in which the disclosure may be implemented, or all the features that may be added to the instant disclosure. For example, features illustrated with respect to one embodiment may be incorporated into other embodiment, and features illustrated with respect to a particular embodiment may be deleted from that embodiment. Thus, the disclosure contemplates that in some embodiments of the disclosure, any feature or combination of features set forth herein can be excluded or omitted. In addition, numerous variations and additions to the various embodiments suggested herein will be apparent to those skilled in the art in light of the instant disclosure, which do not depart from the instant disclosure. In other instances, well-known structures, interfaces, and processes have not been shown in detail in order not to unnecessarily obscure the invention. It is intended that no part of this specification be construed to effect a disavowal of any part of the full scope of the invention. Hence, the following descriptions are intended to illustrate some particular embodiments of the disclosure, and not to exhaustively specify all permutations, combinations and variations thereof.

Unless otherwise defined, all technical and scientific terms used herein have the same meaning as commonly understood by one of ordinary skill in the art to which this disclosure belongs. The terminology used in the description of the disclosure herein is for the purpose of describing particular aspects or embodiments only and is not intended to be limiting of the disclosure.

All publications, patent applications, patents and other references cited herein are incorporated by reference in their entireties for the teachings relevant to the sentence and/or paragraph in which the reference is presented. References to techniques employed herein are intended to refer to the techniques as commonly understood in the art, including variations on those techniques or substitutions of equivalent techniques that would be apparent to one of skill in the art.

U.S. patent application Ser. No. 14/827,375 discloses an apparatus that uses radio frequency (RF) energy to measure the sub-epidermal capacitance using a bipolar sensor, where the sub-epidermal capacitance corresponds to the moisture content of the target region of skin of a patient. The '375 application also discloses an array of these bipolar sensors of various sizes.

U.S. patent application Ser. No. 15/134,110 discloses an apparatus for measuring sub-epidermal moisture (SEM) similar to the device shown in FIG. 3, where the device emits and receives an RF signal at a frequency of 32 kHz through a single coaxial sensor and generates a bioimpedance signal, then converts this signal to a SEM value.

Both U.S. patents application Ser. Nos. 14/827,375 and 15/134,110 are incorporated herein by reference in their entireties. However, the SEM values of this application may be measured by any similar or equivalent devices or techniques that would be apparent to one of skill in the art. For example, a device measuring the SEM values of this application may be a wired device, a wireless device, or a system comprising various components in communication with each other.

Unless the context indicates otherwise, it is specifically intended that the various features of the disclosure described herein can be used in any combination. Moreover, the present disclosure also contemplates that in some embodiments of the disclosure, any feature or combination of features set forth herein can be excluded or omitted.

The methods disclosed herein include and comprise one or more steps or actions for achieving the described method. The method steps and/or actions may be interchanged with one another without departing from the scope of the present disclosure. In other words, unless a specific order of steps or actions is required for proper operation of the embodiment, the order and/or use of specific steps and/or actions may be modified without departing from the scope of the present disclosure.

As used in the description of the disclosure and the appended claims, the singular forms "a," "an" and "the" are intended to include the plural forms as well, unless the context clearly indicates otherwise.

As used herein, "and/or" refers to and encompasses any and all possible combinations of one or more of the associated listed items, as well as the lack of combinations when interpreted in the alternative ("or").

The terms "about" and "approximately" as used herein when referring to a measurable value such as a length, a frequency, or a SEM value and the like, is meant to encompass variations of ±20%, ±10%, ±5%, ±1%, ±0.5%, or even ±0.1% of the specified amount.

As used herein, phrases such as "between X and Y" and "between about X and Y" should be interpreted to include X and Y. As used herein, phrases such as "between about X and Y" mean "between about X and about Y" and phrases such as "from about X to Y" mean "from about X to about Y."

As used herein, the term "sub-epidermal moisture" or "SEM" refers to the increase in tissue fluid and local edema caused by vascular leakiness and other changes that modify the underlying structure of the damaged tissue in the presence of continued pressure on tissue, apoptosis, necrosis, and the inflammatory process.

As used herein, a "patient" may be a human or animal subject.

As used herein, "delta" refers to a calculated difference between two SEM values.

There may be many causes of saddle sores, plenty of confounding elements, and a lot of closely inter-related issues behind the development of a saddle sore. They strike young and old, male or female, amateur or professional without provocation or distinction. Lance Armstrong received a "therapeutic use exemption" for cortisone in 1999, which had shown up in drug screening. Other professional riders have been forced to not compete due to ulcer-related injuries, although it is generally kept very quiet.

FIGS. 1A-1C illustrate a progression of tissue damage toward a pressure ulcer.

FIG. 1A depicts a cross-section of healthy tissue 100, including the stratum corneum and healthy cells in the epidermis/dermis. The center electrode and the toroidal electrode of a SEM scanner are shown in cross-section in contact with the stratum corneum. An illustrative indication of the sensitive region of the SEM Scanner is shown as the oval region. The region has a depth of sensitivity. In some instances, the depth of sensitivity is in the range of 0.14 to 0.16 inches. In some instances, the depth of sensitivity is less than 0.16 inches.

FIG. 1B is an illustrative cross-section of slightly damaged tissue 110. Cellular damage, for example resulting from long-term application of low-level pressure has affected the tissue. Without being limited by theory, some of the cells have ruptured, releasing the fluid contents into an intercellular space. Alternatively, and without being limited by theory, an inflammatory reaction has caused fluid to migrate into the intercellular space. This damage is not visible on the skin surface.

FIG. 1C is an illustrative cross-section 120 of a more advanced level of damage. Without being limited by theory, the tissue is now mostly ruptured cells, which can provide little mechanical structure to carry the continued applied pressure. The tissue thickness is reduced, with the bone now closer to the skin surface. The ruptured cells and intercellular space are compressed, expelling the fluid out of the local tissue as indicated by arrows.

Figure 2:
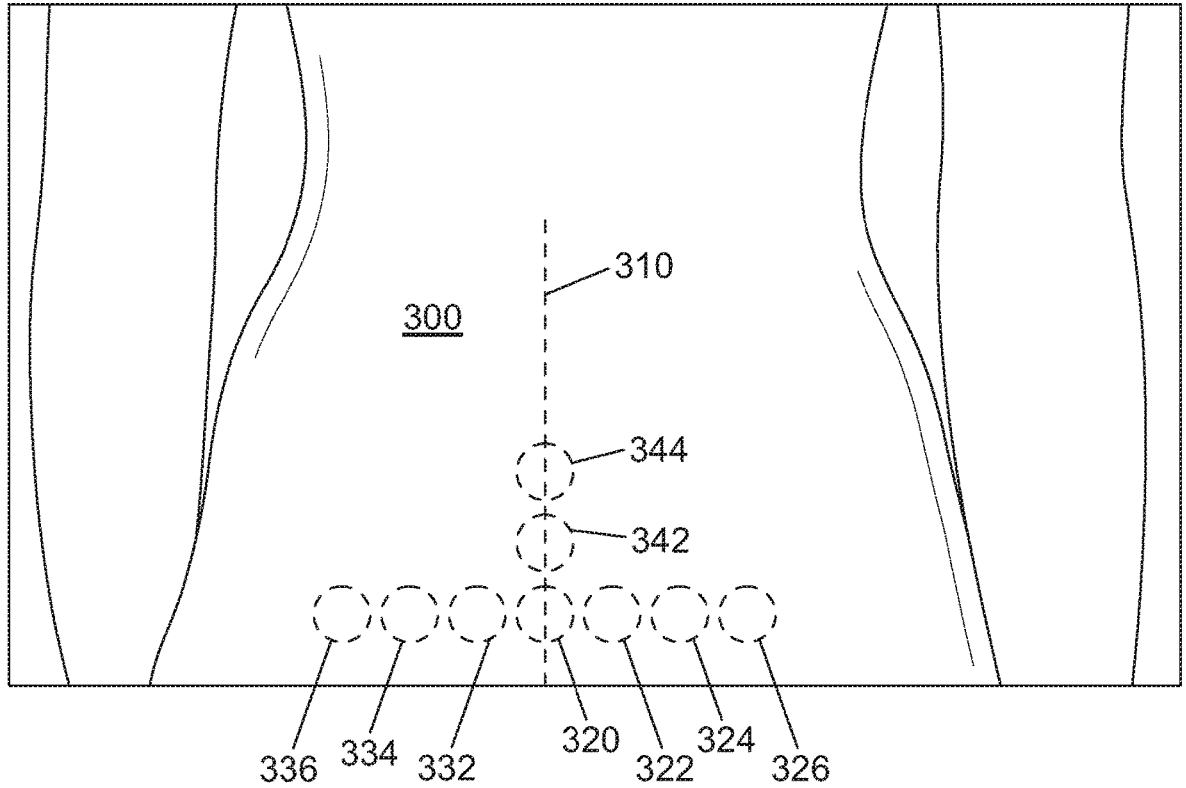
FIG. 2 depicts example locations for SEM measurements on the sacrum, in accordance with the present disclosure.

FIG. 2 depicts example locations for SEM measurements on the sacrum, in accordance with the present disclosure. In an aspect, SEM measurements can be taken around the center positioned at top of gluteal crease 320. In one aspect, centerline 310 can be established from the top of gluteal crease 320. In an aspect, SEM measurements can be taken at locations along centerline 310, for example, at locations 342 and 344. In one aspect, pairs of symmetric SEM measurements can be taken at locations approximately symmetric about centerline 310, for example, at locations 332 and 322, at locations 334 and 324, at locations 336 and 326.

In an aspect, a SEM value is a single SEM measurement. In an aspect, a SEM value is an average SEM measurement generated from SEM measurement values taken at approximately the same location on a patient's skin within a 24-hour period, such as within a 18-hour period, within a 12-hour period, within a 8-hour period, within a 6-hour period, within a 4-hour period, within a 3-hour period, within a 2-hour period, within an hour, within 45 minutes, within 30 minutes, within 15 minutes, within 10 minutes, within 5 minutes, within 1 minute, or within 30 seconds.

Figure 3:
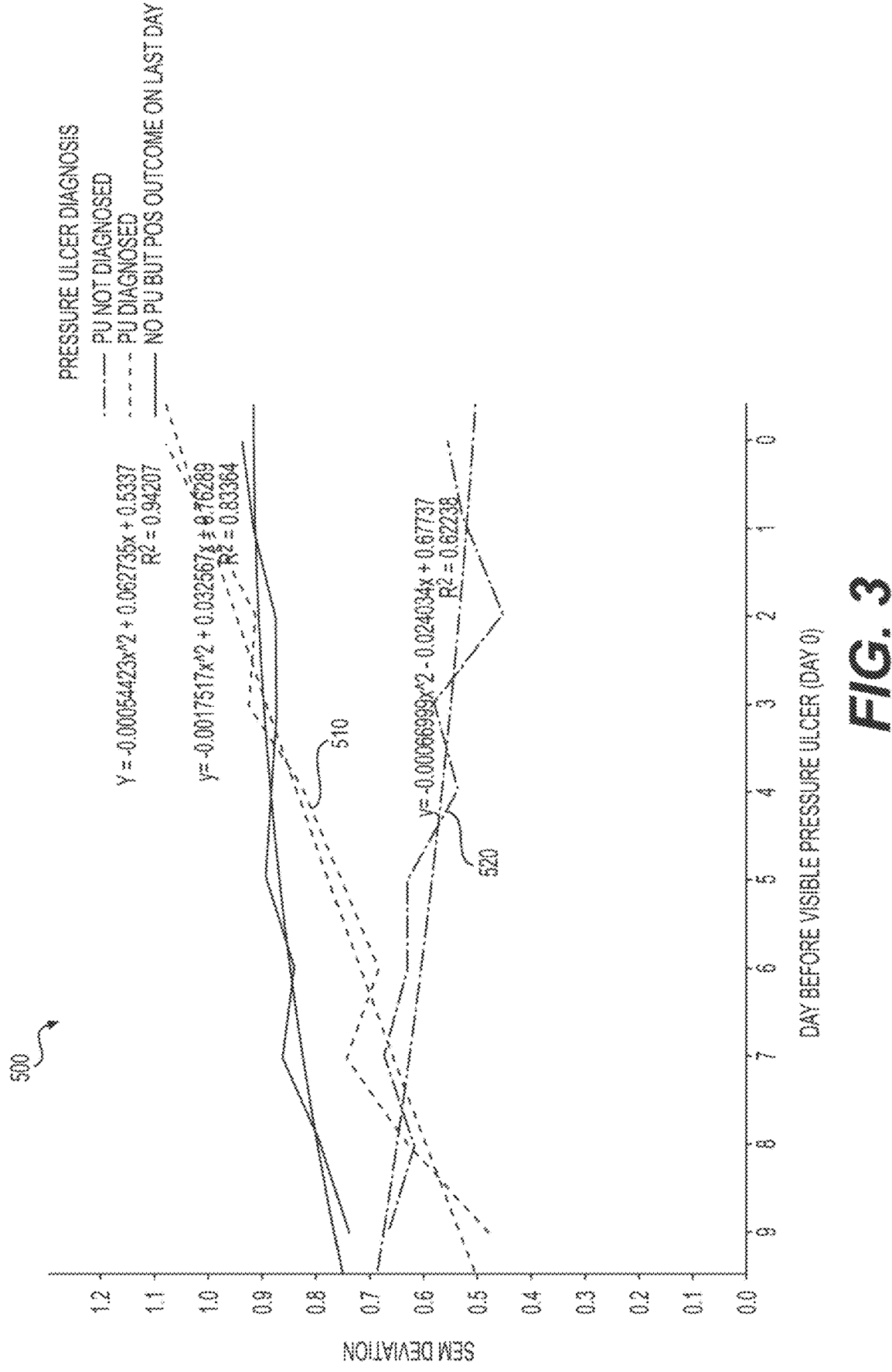
FIG. 3 depicts SEM values over time for patients that do and do not develop pressure ulcers, in accordance with the present disclosure.

FIG. 3 depicts SEM values over time for patients that do and do not develop pressure ulcers, in accordance with the present disclosure. Curve 510 represents average SEM values for the days leading up to a diagnosis of a pressure ulcer on Day 0. The overlaid straight line is a linear approximation. Curve 520 represents average SEM values for the days leading up to a similar set of patients who did not develop a pressure ulcer. In both cases, there was no sign of damage or indication of a future pressure ulcer on the skin. The SEM values were indicative of subsurface damage that was invisible to visual and tactile examination. The overlaid straight line is a linear approximation.

Figure 4:
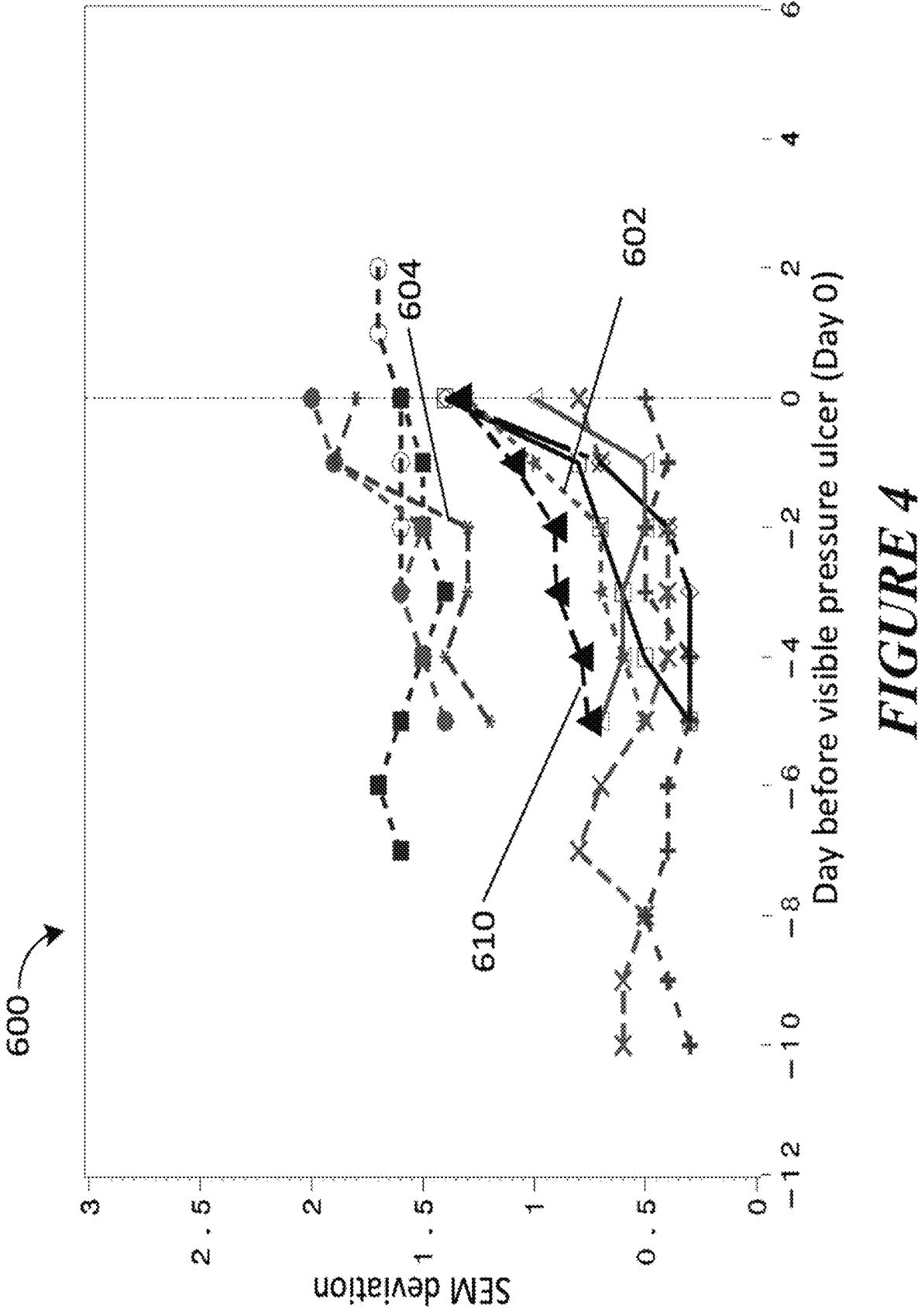
FIG. 4 depicts SEM delta values over time for patients that develop pressure ulcers, in accordance with the present disclosure.

FIG. 4 depicts SEM delta values over time for patients that develop pressure ulcers, in accordance with the present disclosure. Curves 602 and 604 illustrate the acceleration of the rate of increase, i.e. the slope, of the curve as time gets closer to the point at which a visual examination leads to a clinical diagnosis. Curve 610 is an average of the other curves and shows the upward curve, i.e. acceleration of the rate of increase.

Figure 5:
FIG. 5 depicts illustrative SEM values and delta values over time for patients that develop pressure ulcers, in accordance with the present disclosure.

FIG. 5 is an example plot of measured and computed SEM values, in accordance with the present disclosure. Curve 910 is a set of SEM values for a skin area that is prone to development of a pressure ulcer. Curve 920 is a matching set of SEM values for a second skin area that is near the first area but not at risk for a pressure ulcer. Curve 920 serves as a reference. Curve 930 is a "delta" SEM value calculated by subtracting the reference value of curve 920 from the matching SEM value of curve 910.

Tissue damage may be detected in several ways. In one aspect, the slope of the SEM curve 910, for example the slope between points 914 and 916, is compared against a threshold slope, indicated by line 912. If the slope of the curve 910 exceeds the slope of line 912, this indicates a degree of damage. There may be multiple slopes used to evaluate multiple degrees of tissue damage. In one aspect, a slope is determined with respect to any two points on SEM curve 910, and is compared to the slope of line 912 to indicate a degree of damage. In an aspect, the slope of line 912 is determined by the health history of the subject. In one aspect, the curvature of a SEM curve is compared to a threshold curvature, where an over-curvature indicates a degree of damage.

In an aspect, the value of the delta curve 930 is compared to a threshold level 938. When curve 930 exceeds threshold 938, for example at point 936, this indicates a degrees of damage. There may be multiple thresholds used to evaluate multiple levels of tissue damage.

In an aspect, a threshold may be about 0.3, 0.35, 0.4, 0.45, 0.5, 0.55, 0.6, 0.65, 0.7, 0.75, 0.8, 0.85, 0.9, 0.95, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, or 7.5. In one aspect, a threshold may range from 0.1 to 8.0, such as from 0.1 to 1.0, from 1.1 to 2.0, from 2.1 to 3.0, from 3.1 to 4.0, from 4.1 to 5.0, from 5.1 to 6.0, from 6.1 to 7.0, from 7.1 to 8.0, from 0.1 to 7.5, from 0.5 to 8.0, from 1.0 to 7.0, from 1.5 to 6.5, from 2.0 to 6.0, from 3.0 to 5.5, from 3.5 to 5.0, or from 4.0 to 4.5. In an aspect, a threshold can be scaled by a factor or a multiple based on the values provided herein. It will be understood that a threshold is not limited by design, but rather, one of ordinary skill in the art would be capable of choosing a predetermined value based on a given unit of SEM. In one aspect, thresholds of the present disclosure are varied according to the specific portion of a patient's body on which measurements are being made, or one or more characteristics of the patient such as age, height, weight, family history, ethnic group, and other physical characteristics or medical conditions.

In one aspect, the slope of the delta curve 930, for example the slope between points 934 and 936, is compared against a threshold slope, indicated by line 932. If the slope of the curve 930 exceeds the slope of line 932, this indicates a degree of damage. There may be multiple slopes used to evaluate multiple degrees of tissue damage. In one aspect, a slope is determined with respect to any two points on delta curve 930, and is compared to the slope of line 932 to indicate a degree of damage. In an aspect, the slope of line 932 is determined by the health history of the subject. In one aspect, the curvature of a delta curve is compared to a threshold curvature, where an over-curvature indicates a degree of damage.

In an aspect, a SEM delta value above a predefined threshold value is an indication of sub-epidermal damage that may lead to a pressure ulcer. The time interval between the time when the SEM delta value first equals or exceeds this threshold and the development of visible symptoms of a pressure ulcer may be a first duration when the SEM delta value increases linearly. A first duration may be 5 or more days, such as 6 or more days, 7 or more days, 8 or more days, 9 or more days, or 10 or more days.

In another aspect, when the SEM delta curve shows an upward curvature or other deviation above a linear progression, the visible symptoms may be present within a shorter amount of time, for example 2-3 days, 1-4 days. 1-3 days, 1-2 days, or 2-4 days. In an aspect, the SEM scanner, which includes an SEM sensor and electronics to measure the capacitance of the SEM sensor and convert this measured capacitance to a SEM value and store a plurality of these SEM values then calculate and display a SEM delta value from the plurality of SEM values and transmit a portion of the measurements and delta values to a remote computer, is used to generate a SEM delta value for a particular location on the patient's skin, for example the heel. These SEM delta values are tracked and the trend of the SEM delta values, i.e. the slope and curvature of a curve connecting these SEM delta values, is analyzed. In an aspect, the amount by which an incremental SEM delta value is above a linear prediction based on prior SEM delta values is compared to a predetermined threshold. In an aspect, the amount by which an incremental SEM delta value is above the most recent prior SEM delta value is compared to a predetermined threshold. In an aspect, a curvature of the best-fit curve fitted to a predefined number of the most-recent SEM delta values is compared to a predetermined threshold. In an aspect, the number of sequential SEM delta values that exceeds a predetermined value threshold is compared to a number-of-readings threshold. In each of these aspects, the SEM scanner provides a notification when the comparison parameter exceeds the respective threshold.

In an aspect, the trend analysis may ignore a single SEM delta value that is below a threshold if both the prior and subsequent SEM delta values are above the threshold.

In an aspect, the trend curve of the SEM delta values is a point-to-point linear connection. In an aspect, the trend curve is a best-fit curve fitted to the SEM delta values. In an aspect, the fitted curve is required to intersection the most-recent SEM delta value.

From the foregoing, it will be appreciated that the present disclosure can be embodied in various ways, which include but are not limited to the following:

Embodiment 1. A method of detecting tissue damage before it is visible on a patient's skin, comprising: measuring a plurality of sub-epidermal moisture (SEM) values at a single location at incremental times, calculating a slope between the latest SEM value and the immediately prior SEM value, comparing this slope to a threshold value, and determining that there is tissue damage if the slope exceeds the threshold value.

Embodiment 2. A method of detecting tissue damage before it is visible on a patient's skin, comprising: measuring a plurality sub-epidermal moisture (SEM) values at a plurality of locations at incremental times, calculating a delta value for the plurality of SEM values for each time, calculating a slope between the latest delta value and the immediately prior delta value, comparing this slope to a threshold value, and determining that there is tissue damage if the slope exceeds the threshold value.

Embodiment 3. A method of detecting tissue damage before it is visible on a patient's skin, comprising: measuring a plurality of sub-epidermal moisture (SEM) values at a single location at each of a plurality of incremental times, calculating a SEM delta value for each incremental time, fitting a curve to a predetermined number of the most-recent SEM delta values, calculating a curvature of the fitted curve, comparing this curvature to a threshold value, and determining that there is tissue damage if the curvature exceeds the threshold value.

Having now generally described the invention, the same will be more readily understood through reference to the following examples that are provided by way of illustration, and are not intended to be limiting of the present disclosure, unless specified.

EXAMPLES

Example 1: SEM Delta Trends in Heels of Patients is Indicative of Pressure Ulcer Onset SEM measurements are taken over time at the heels of patients using an apparatus according to the present disclosure, prior to any visual diagnosis of pressure ulcers at the heel. At each time point, each of the patients is directed to have toes pointed away from the body and rotated outwards toward the lateral side of the body. A sensor of the apparatus is placed on the medial side of the heel. The sensor is adjusted for full contact with the heel, and multiple measurements are taken around the back of the heel in a curve. Each of the SEM measurements is converted to a SEM delta value by subtracting from the measurement a reference SEM value obtained from another body part of the same patient that is not experiencing external pressure or mechanical forces. The resulting SEM delta values in a single day are averaged and plotted for each patient.

Figure 6:
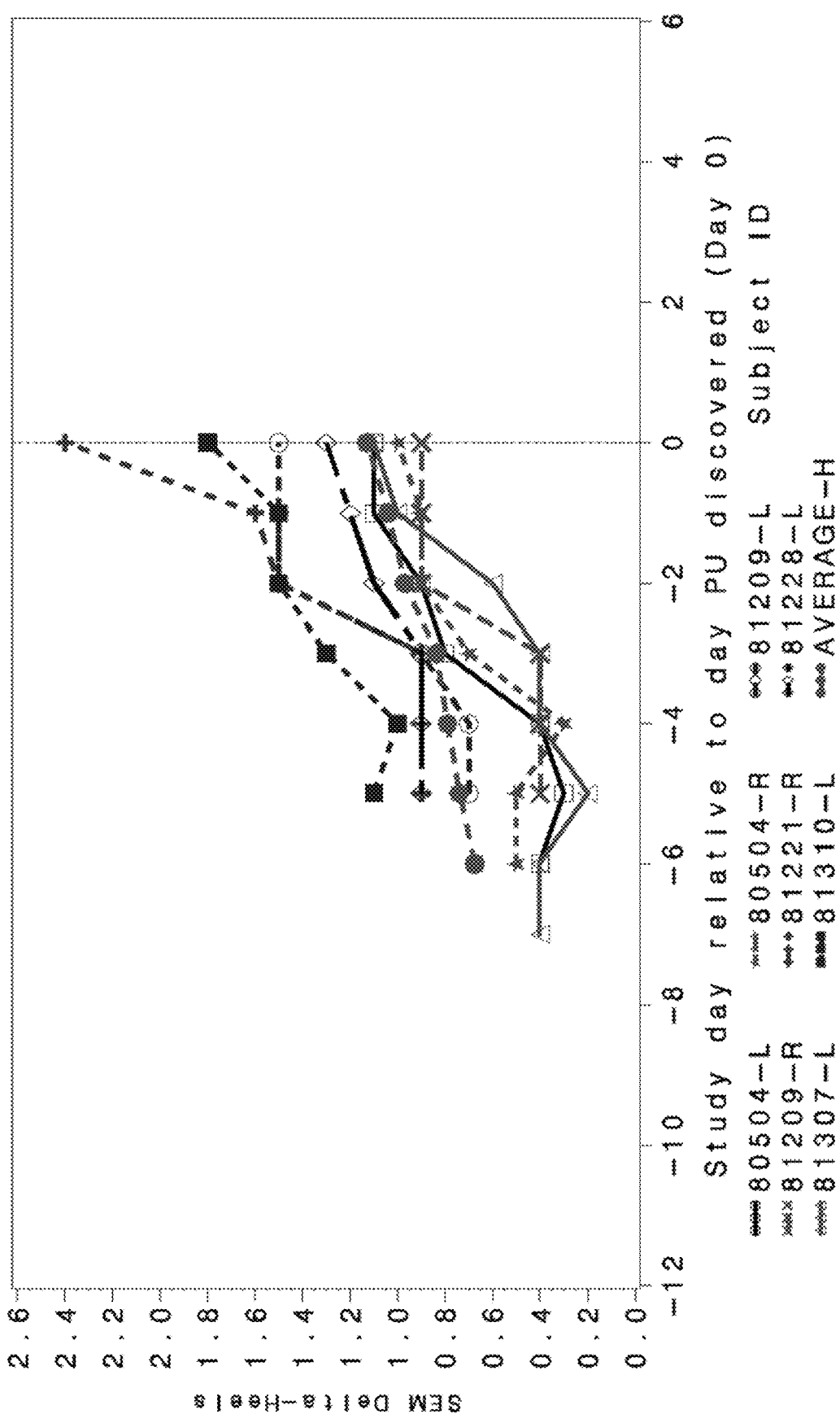
FIG. 6 depicts example SEM delta values over time for patients that develop pressure ulcers in the heels, in accordance with the present disclosure.

FIG. 6 illustrates trends of SEM delta values for seven (7) patients prior to a pressure ulcer diagnosis at one or both of their heels. Trends across different patients are time-shifted to align to Day 0 as the pressure ulcer diagnosis event. A reference SEM delta curve ("AVERAGE-H") is generated by averaging the SEM delta values trends of all patients (n=20) that are eventually visually diagnosed with a heel pressure ulcer. As shown in FIG. 6, the SEM delta values of these seven patients exhibit a spike in magnitude two (−2) to four (−4) days prior to the visual diagnosis compared to the reference curve. For these patients, a steeper slope of the SEM delta value trend compared to the reference curve is indicative of early onset of a pressure ulcer before any visual detection.

I claim:

1. A method of detecting sub-epidermal damage, comprising:

(a) obtaining a plurality of sub-epidermal moisture (SEM) values at a single location on a patient's skin at incremental timepoints over a period of time using a SEM scanner, wherein the SEM scanner comprises: (i) one or more bipolar sensors configured to measure tissue biocapacitance indicative of SEM, (ii) a processor configured to receive the plurality of SEM value, and (iii) a non-transitory computer-readable medium electronically coupled to the processor, (b) receiving in the processor the plurality of SEM values, (c) calculating a rate of change between the most recent SEM value at a second point in time and the immediately prior SEM value at a first point in time, (d) comparing the rate of change to a threshold rate of change, wherein the threshold rate of change is based on one or more characteristics of the patient selected from the group consisting of: age, height, weight, family history, ethnic group, health history, and other physical characteristics or medical conditions, (e) detecting tissue damage below the surface of the patient's skin when the rate of change exceeds the threshold rate of change, wherein the detecting occurs between 1 to 10 days before the tissue damage is visible on the surface of the patient's skin, and (f) displaying a notification on the SEM scanner when the rate of change exceeds the threshold rate of change, wherein the non-transitory computer-readable medium electronically comprises instructions stored thereon that, when executed on the processor, perform the steps of: (c), (d), (e), and (f).

2. The method of claim 1, wherein the threshold rate of increase is based on the specific portion of the patient's body on which measurements are being made.

3. A method of detecting sub-epidermal damage, comprising:

(a) obtaining a plurality of sub-epidermal moisture (SEM) values at a plurality of locations on a patient's skin at incremental timepoints over a period of time using a SEM scanner, wherein the SEM scanner comprises: (i) one or more bipolar sensors configured to measure tissue biocapacitance indicative of SEM, (ii) a processor configured to receive the plurality of SEM value, (iii) a non-transitory computer-readable medium electronically coupled to the processor, (b) receiving in the processor the plurality of SEM values, (c) calculating an average delta value for the plurality of SEM values at each incremental timepoint over a first period of time and a second period of time, (d) calculating a rate of change between the most recent average delta value over the second period of time and the immediately prior average delta value over the first period of time, (e) comparing the rate of change to a threshold rate of change, wherein the threshold rate of change is based on one or more characteristics of the patient selected from the group consisting of: age, height, weight, family history, ethnic group, health history, and other physical characteristics or medical conditions, (f) detecting tissue damage below the surface of the patient's skin when the rate of change exceeds the threshold rate of change, wherein the detecting occurs between 1 to 10 days before the tissue damage is visible on the surface of the patient's skin, and (g) displaying a notification on the SEM scanner when the rate of change exceeds the threshold rate of increase, wherein the non-transitory computer-readable medium electronically comprises instructions stored thereon that, when executed on the processor, perform the steps of: (c), (d), (e), (f), and (g).

4. The method of claim 3, wherein the threshold rate of increase is based on the specific portion of the patient's body on which measurements are being made.

5. A method of detecting sub-epidermal damage, comprising:

(a) obtaining a plurality of sub-epidermal moisture (SEM) values at a single location on a patient's skin at incremental timepoints over a period of time using a SEM scanner, wherein the SEM scanner comprises: (i) one or more bipolar sensors configured to measure tissue biocapacitance indicative of SEM, (ii) a processor configured to receive the plurality of SEM value, and (iii) a non-transitory computer-readable medium electronically coupled to the processor, (b) receiving in the processor the plurality of SEM values, (c) calculating a delta value for each incremental time-point, (d) fitting a curve to more than two of the most-recent delta values, (e) calculating a curvature of the fitted curve, (f) comparing the curvature to a threshold curvature, wherein the threshold curvature is based on one or more characteristics of the patient selected from the group consisting of: age, height, weight, family history, ethnic group, health history, and other physical characteristics or medical conditions, (g) detecting tissue damage below the surface of the patient's skin when the curvature exceeds the threshold curvature, wherein the detecting occurs between 1 to 10 days before the tissue damage is visible on the surface of the patient's skin, and (h) displaying a notification on the SEM scanner when the curvature exceeds the threshold curvature, wherein the non-transitory computer-readable medium electronically comprises instructions stored thereon that, when executed on the processor, perform the steps of: (c), (d), (e), (f), (g), and (h).

6. The method of claim 5, wherein the threshold curvature is based on the specific portion of the patient's body on which measurements are being made.

\* \* \* \* \*